(12) United States Patent
Ostgard et al.

(10) Patent No.: US 6,486,366 B1
(45) Date of Patent: Nov. 26, 2002

(54) METHOD FOR PRODUCING ALCOHOLS BY HYDROGENATION OF CARBONYL COMPOUNDS

(75) Inventors: Daniel Ostgard, Kleinostheim (DE); Monika Berweiler, Maintal (DE); Stefan Röder, Sinntal (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 10/024,487

(22) Filed: Dec. 21, 2001

(30) Foreign Application Priority Data

Dec. 23, 2000 (DE) .......................................... 100 65 029
Oct. 31, 2001 (WO) .............................. PCT/EP01/12567

(51) Int. Cl.[7] .............................................. C07C 27/00
(52) U.S. Cl. ...................... 568/863; 568/862; 568/864; 568/881; 568/885
(58) Field of Search ................................. 568/862, 863, 568/864, 881, 885

(56) References Cited

U.S. PATENT DOCUMENTS 3,347,798 A * 10/1967 Baer
3,429,654 A * 2/1969 Friedrichsen
3,538,018 A * 11/1970 Pilch
3,798,176 A * 3/1974 Ao
4,153,578 A 5/1979 De Thomas et al. ........ 252/438
4,576,926 A * 3/1986 Wang
4,637,990 A * 1/1987 Torobin
4,917,857 A * 4/1990 Jaeckel

FOREIGN PATENT DOCUMENTS

| DE | 2 053 799 | 6/1971 |
| DE | 2 101 856 | 7/1972 |
| DE | 2 100 373 | 9/1972 |

* cited by examiner

*Primary Examiner*—Michael L. Shippen
(74) *Attorney, Agent, or Firm*—Smith, Gambrell & Russell, LLP

(57) ABSTRACT

A method for preparation of alcohols by catalytic hydrogenation of carbonyl compounds with hydrogen or hydrogen-containing gases in the presence of a hydrogenation catalyst of Raney type, where the catalyst is used in the form of hollow bodies, Preferred as catalytically active components are nickel, cobalt, copper, iron, platinum, palladium or ruthenium.

35 Claims, No Drawings

METHOD FOR PRODUCING ALCOHOLS BY HYDROGENATION OF CARBONYL COMPOUNDS

INTRODUCTION AND BACKGROUND

The invention is directed toward an improved method for producing alcohols from carbonyl compounds that includes catalytic hydrogenation of carbonyl compounds with hydrogen or hydrogen-containing gases in the presence of a molded hydrogenation catalyst of Raney type. The invention especially concerns the production of sugar alcohols. The method allows the use of distinctly lower amounts of catalyst in the production of alcohols while having the same or higher yields than with the methods known up to now.

In accordance with this invention all organic compounds that contain a C=O group, including those compounds that contain an O=C—O group, are seen as carbonyl compounds. Thus, ketones, aldehydes, carboxylic acids, carboxylates, carboxylic anhydrides, carboxylic acid esters, carboxylic acid amides and carboxylic acid halides are meant by the term carbonyl compounds.

Alcohols are a decidedly important class of substances in organic chemistry. They serve, for example, as starting materials for the production of solvents, surfactants, perfumes, flavorings, additives, drugs and other organic substances. Moreover, they are very important as monomers for various plastics. Sugar alcohols are widely used, for example, as sugar substitutes.

In the production of alcohols by hydrogenation [of] carbonyl compounds Raney catalysts are frequently preferred because of their good catalytic properties and because they are significantly easier to make than supported catalysts. Raney catalysts, which are also called activated metal catalysts, consist of an alloy of at least one catalytically active metal and at least one metal that can be leached out by alkalis. Chiefly aluminum is used as the alkali-soluble alloy component, but other metals like zinc and silicon can also be used. By adding alkalis to the alloy the leachable component is dissolved out, due to which the catalyst becomes activated.

Numerous inventions for producing alcohols from carbonyl compounds by catalytic hydrogenation with Raney catalysts are known. In each case according to the process, various Raney catalysts, more precisely catalysts with different active metals or combinations of metals, are used.

EP 0 724 908 describes a method for producing alcohols from carbonyl compounds in which Raney catalysts whose catalytically active component is a noble metal are used as hydrogenation catalysts. The catalysts are used in powder form.

Raney catalysts in powder form have the disadvantage that they can only be used in batch processes, and have to be separated from the reaction medium after the catalytic conversion, at high cost. Because of this, among other things, it is preferable to carry out the production of alcohols by hydrogenation of carbonyl compounds using molded Raney catalysts and as far as possible in a continuous process. Fixed bed catalysts, which also have to have sufficient strength for continuous operation, in addition to having good catalytic activity, are necessary for this purpose.

JP 07206737 A2 describes another method for producing alcohols by catalytic hydrogenation of carbonyl compounds. The catalysts used in this method are spherical Raney catalysts based on copper, which preferably also contain iron and, as leachable component, aluminum. The method can be run using a fixed catalyst bed.

EP 0 773 063 describes a method for producing sugar alcohols using a fixed catalyst bed in which a Raney nickel catalyst is used. The use of a nodular Raney catalyst produced by dripping the liquid alloy into a liquid, preferably water, is important in accordance with this invention.

Sugars are hydrogenated by the method described in EP 0 854 149, likewise continuously and using a fixed catalyst bed. The catalysts used with this method are produced by mixing a catalyst alloy and a metal that serves as binder and then pressure molding this mixture to form molded pieces. After drying and calcination, these molded pieces are activated by treatment with aqueous alkalis. This produces a catalyst that consists of a catalytically active shell and a largely catalytically inactive core. It is necessary to use the binder in order to give the catalyst the necessary mechanical stability.

A serious disadvantage of the methods noted in the documents JP 07206737 A2, EP 0 773 063 and EP 0 854 149 for producing various alcohols by hydrogenation of carbonyl compounds lies in the high bulk density of the Raney catalysts. Because of this, these catalysts have relatively low activity with respect to the weight of catalytically active metal that is used.

Another disadvantage is that the reactors that are used have to have high stability. This requires additional investments in the construction and operation of a hydrogenation plant.

Metal catalysts in the form of hollow bodies, preferably in the form of hollow spheres, are described in DE 199 33 450.1. These catalysts have a low bulk density, from 0.3 to 1.3 g/mL. Besides the catalysts, the use of these catalysts in hydrogenation reactions is also claimed. The examples [in this document] give activity tests for hydrogenation of nitrobenzene to aniline, in which the hydrogen uptake and thus the activity of the catalyst per gram of catalyst is clearly higher when the hollow spherical catalysts are used than when a comparison catalyst is used. However, the use of the described catalysts for production of alcohols by hydrogenation of carbonyl compounds is not mentioned.

For this reason the task of this invention is to develop a method for producing alcohols from carbonyl compounds by catalytic hydrogenation in which the disadvantages of the said methods do not arise. Another goal of the invention is to achieve the same or better starting material conversion rates by comparison with the known methods while using less catalyst material.

The task underlying the invention is solved by the fact that alcohols can be produced by hydrogenation of carbonyl compounds with distinctly higher conversion rates per unit of weight of catalyst if hollow Raney catalysts are used than with the known catalysts. This observation is surprising in that one cannot necessarily assume that the hollow Raney catalysts achieve the necessary activities in the particular case of the hydrogenation of carbonyl compounds.

The object of the invention is a method for producing alcohols by catalytic hydrogenation of carbonyl compounds with hydrogen or hydrogen-containing gases in the presence of a molded hydrogenation catalyst of the Raney type, which is characterized by the fact that the Raney catalyst is in the form of hollow bodies. This method has the advantage that alcohols can be produced with the same or higher yields while using clearly lesser amounts of catalyst than was possible up to now according to the prior art.

SUMMARY OF THE INVENTION

The advantage underlying this invention is achieved through the use of Raney catalysts in the form of hollow bodies. The production of the catalysts used in the method in accordance with the invention can be carried out in correspondence with the method described in DE 199 33 450.1. According to this method, a mixture of an alloy powder of a catalytically active metal and a leachable metal, preferably aluminum, an organic binder and optionally an inorganic binder, water and promoters is deposited onto spheres that consist of a thermally removable material. Preferably, polystyrene foam spheres can be used. The deposition of the mixture containing the metal alloy onto the polymer spheres can preferably be carried out in a fluidized bed. Preferably, 0–10 wt % polyvinyl alcohol and/or 0–3 wt % glycerol can be used as organic binders. The coated polymer foam spheres are then calcined at a temperature above 300° C., preferably in a range from 450 to 1300° C., in order to remove the polymer foam thermally and to sinter the metal. In this way the hollow spheres obtain a stable shape. After calcination the hollow spherical catalysts are activated by treatment with basic solutions, preferably alkali or alkaline earth hydroxides in water, more preferably aqueous sodium hydroxide. The resulting catalysts have bulk densitys between 0.3 and 1.3 kg/L.

DETAILED DESCRIPTION OF THE INVENTION

For the method in accordance with the invention it is preferred that the hollow spherical Raney catalysts contain nickel, cobalt, copper, iron, platinum, palladium, ruthenium or mixtures of these metals as catalytically active components.

Preferably, Raney nickel catalysts that have been activated by leaching out of aluminum, silicon and/or zinc, especially aluminum, by means of alkalis, are used in the production of alcohols in accordance with the invention.

The method is carried out in accordance with the invention with catalysts in the form of hollow bodies. It is preferred that the Raney catalyst be in the form of hollow spheres. Hollow spheres are usually easy to produce and have high resistance to breakage.

Another advantage of the method in accordance with the invention lies in the fact that the Raney catalysts that are used have lower bulk density than the Raney catalysts for hydrogenation of carbonyl compounds known from the prior art. It is advantageous for the bulk density of the Raney catalysts that are used to lie in the range from 0.3 g/mL to 1.3 g/mL.

If molded catalyst bodies that are too large are used, it is possible that the educt to be hydrogenated will not sufficiently come into contact with the catalyst. A catalyst particle size that is too small will lead to a very large, possibly too great, pressure loss occurring in a continuous process.

For this reason it is preferred that the catalyst molded bodies that are used have a diameter in the range from 0.05 to 20 mm.

So that the catalysts that are used in the method in accordance with the invention will have, on the one hand, sufficient strength and, on the other, low bulk density, it is preferred that the catalyst molded bodies that are used have a shell thickness in the range from 0.05 to 7 mm, preferably 0.1 mm to 5 mm.

The catalyst shells can be impermeable or can have a porosity from 0 up to 80% and higher.

Hollow catalysts that consist of one or more layers can be used in the method in accordance with the invention. If the catalyst molded bodies have more than one layer, the molded bodies are dried between the individual coating steps in producing them. This is preferably carried out in a fluidized bed at temperatures from 60 to 150° C.

It is possible for the catalyst molded bodies used in the method to contain an inorganic binder. The binder allows the catalyst molded bodies to have higher strength, which is necessary because of their hollow shape. Preferably, powders of the metals that are also contained in the catalyst alloy as catalytically active components are added as binders in producing the catalyst hollow bodies. However, it is also possible to add other binders, especially other metals, as binders.

Frequently it is also advantageous for the catalyst molded bodies used in the method not to contain any binders. If cobalt catalysts are used in accordance with the invention to produce the alcohols, these catalysts are preferably used without binders. Hollow cobalt catalysts have sufficient strength even without added binders.

The catalyst alloy of the catalysts used in accordance with the invention is preferably composed of up to 20–80 wt % of one or more catalytically active metals and up to 20–80 wt % of one or more alkali-leachable metals, preferably aluminum. A fast or slowly cooled alloy can be used as the catalyst alloy. Fast cooling is understood to mean, for example, cooling at a rate from 10 to $10^5$ K/sec. Cooling media can be various gases or liquids such as water. Slow cooling is understood to mean methods with slower cooling rates.

In the method in accordance with the invention it is possible to use hollow Raney catalysts doped with other metals. The doping metals are frequently also called promoters. The doping of Raney catalysts is described, for example, in U.S. Pat. No. 4,153,578, DE 21 01 856, DE 21 00 373 or DE 20 53 799. The cobalt catalyst that is used can preferably be doped with one or more of the elements from groups 3B through 7B, 8 and 1B of the periodic system, especially chromium, manganese, iron, vanadium, tantalum, titanium, tungsten, molybdenum, rhenium and/or metals of the platinum group. It is also possible for the cobalt catalyst that is used to be doped with one or more elements from groups 1A, 2A, 2B and/or 3A of the periodic system and/or germanium, tin, lead, antimony or bismuth. The amount of promoters in the catalyst can preferably be 0–20 wt %. The promoters can already be contained as an alloy in component or can be added only later, especially after activation.

During the method in accordance with the invention the hollow Raney catalysts are used in the activated form. The leachable metal present in the unactivated catalyst particle can in the activated state have been leached out with alkalis entirely or only partially.

The method in accordance with the invention can be carried out with hydrogen as the hydrogenation gas or with gas mixtures that contain hydrogen, for example, a mixture of hydrogen and carbon monoxide and/or carbon dioxide. In order to avoid possible poisoning of the catalyst, it is preferable to carry out the method in accordance with the invention with a gas or gas mixture that contains at least 95%, preferably at least 99% hydrogen.

The method enables the production of more or less pure individual substances and also the production of mixtures of different alcohols. Especially in the production of chiral alcohols, for example, by hydrogenation of asymmetric ketones, product mixtures of different enantiomers or diastereomers can be obtained.

It is preferred that the hydrogenation be carried out in a fixed bed or suspension reactor in continuous operation. However, the invention also provides for hydrogenation to be carried out in a batch process. In a continuous process the reactor can be operated in a soaking bed or trickle bed process, with the trickle bed process being preferred.

The method in accordance with the invention can be carried out with ketones, aldehydes, carboxylic acids, carboxylates, carboxylic acid anhydrides, carboxylic acid esters, carboxylic acid amides and/or carboxylic acid halides. The choice of appropriate starting compound is dependent, among other things, on the desired product. The starting compound must be chosen so that the desired product can be obtained by the hydrogenation of one or more carbonyl groups and possibly the hydrogenation of other groups that are subject to hydrogenation. The choice of suitable starting compound is also dependent, among other things, on what starting product is more readily available. For instance, in one case it may be preferable to produce an alcohol by hydrogenation of an aldehyde, since the aldehyde is more readily available than a corresponding carboxylic acid amide. In contrast, in other cases it may be better to start from the corresponding carboxylic acid amide. However, independent of the desired alcohol, the preparation is basically possible starting with all of the listed carbonyl compounds. The desired, especially the preferred alcohols listed further below, can thus in principle be produced from a ketone, aldehyde, carboxylic acid, carboxylate, carboxylic acid anhydride, open-chain and cyclic carboxylic acid esters, open-chain and cyclic carboxylic acid amides and/or carboxylic acid halide that leads to the desired alcohol. The relevant compounds can be aliphatic, aromatic, alicyclic and aromatic-aliphatic compounds with one, two, three or more C=O groups.

Some examples of starting materials for the method for producing alcohols in accordance with the invention, which however do not limit the method in accordance with the invention to the starting materials, are: acetic acid, propionic acid, butyric acid, pentanoic acid, hexanoic acid, heptanoic acid, octanoic acid, nonanoic acid, stearic acid, lauric acid, pivalic acid, isobutyric acid, oxalic acid, malonic acid, maleic acid, succinic acid, glutaric acid, adipic acid, crotonic acid, benzoic acid, o-chlorobenzoic acid, m-chlorobenzoic acid, p-chlorobenzoic acid, m-fluorobenzoic acid, p-fluorobenzoic acid, methylbenzoic acid, o-hydroxybenzoic acid, m-hydroxybenzoic acid, p-hydroxybenzoic acid, phthalic acid, terephthalic acid, isophthalic acid, naphthalenedicarboxylic acid, phenoxybenzoic acid, cyclohexanecarboxylic acid, the methyl and ethyl esters and amides of the said acids, benzaldehyde, propionaldehyde, acetaldehyde, propionaldehyde, acetone, benzophenone, γ-butyrolactone, ε-caprolactone, maleic anhydride, phthalic anhydride, glucose, xylose, lactose, fructose, 3-hydroxypropionaldehyde.

Aliphatic and aromatic alcohols and alcohols with aromatic and aliphatic groups can be prepared from the underlying carbonyl compounds using the method in accordance with the invention. The alcohols can be primary and secondary alcohols. The products can be alcohols with the general formula

$R^1R^2CH$—OH where $R^1$ and $R^2$, independent of one another, are aliphatic and/or aromatic, unbranched and/or branched, substituted and/or unsubstituted, saturated and/or unsaturated residues or hydrogen. The alcohols produced in accordance with the invention can be open-chain or alicyclic alcohols or alcohols containing aromatic groups.

It is preferred that one obtain as product alcohols with the general formula $R^1R^2CH$—OH, where $R^1$ and $R^2$, independent of one another, are methyl, ethyl, n-propyl, isopropyl, n-butyl, isobutyl, tert-butyl, n-pentyl, isopentyl, n-heptyl, n-octyl, isooctyl, n-nonyl, n-decyl, n-undecyl and/or n-dodecyl residues and/or residues of the general formula $H_3C$—$(CH_2)_n$, where n is a whole number from 11 to 30, or hydrogen. Preferred as starting material are the aldehydes, ketones, carboxylic acids, carboxylates, open-chain esters, especially methyl and ethyl esters, and not or [sic] N-alkylated carboxylic acid amides.

It is further possible for the residues $R^1$ and/or $R^2$ to be substituted with one or more residues from the series F, Cl, Br, I, $NO_2$, $NH_2$, OH, CN, alkyl, aryl, alkenyl, alkynyl, O=C, HOOC, $H_2NOC$, ROOC, RO with R=alkyl, aryl, alkenyl or alkynyl.

It is possible for one to obtain as products alcohols that contain two or more hydroxyl groups. These alcohols can be obtained by hydrogenation of carbonyl compounds that have two or more C=O groups and optionally already have hydroxyl groups or by hydrogenation of carbonyl groups that have only one C=O group and at least one hydroxyl group.

Likewise preferred is the preparation of alcohols with the general formula Ar—$(CH_2)_{CR}{}^3H$—OH, where Ar is a mononuclear aromatic residue substituted zero, one, two, three, four or five times, or a polynuclear aromatic residue substituted any number of times, m is a whole number between 0 and 20 and $R^3$ is a substituted or unsubstituted alkyl, cycloalkyl, aryl, alkenyl or alkynyl residue. Possible substituents for the aromatic residue Ar and/or the residue $R^3$ are F, Cl, Br, I, $NO_2$, $NH_2$, HO, CN, alkyl, especially methyl and ethyl, aryl, alkenyl, alkynyl, O=C, HOOC, $H_2NOC$, $R^3OOC$ and/or RO residues.

Diols of the general formula HO—$(CH_2)p$—OH, where p is a whole number between 2 and 30, especially such diols with p=2, 3, 4, 5, 6, 7 and 8, are preferred. Preferably these alcohols are prepared from the underlying hydroxy aldehydes, hydroxycarboxylic acids, hydroxycarboxylates, hydroxycarboxylic acid amides, hydroxycarboxylic acid esters, dialdehydes, dicarboxylic acids, dicarboxylates, dicarboxylic acid amides and/or dicarboxylic acid esters or cyclic esters (lactones) that have the same number of carbon atoms. For example, 1,4-butanediol can be produced by hydrogenation of γ-butyrolactone, 4-hydroxybutyraldehyde or succinic anhydride.

A likewise preferred embodiment of the method in accordance with the invention is the production of substituted and unsubstituted diols, sugar alcohols and polyalcohols of the general formula $R^4H(OH)C$—$(C(OR^5)R^6)q$—$C(OR^9)R^7R^8$, where $R^4$, $R^6$, $R^7$ and $R^8$, independent of one another, can be F, Cl, Br, I, $NO_2$, $NH_2$, HO, CN, alkyl, aryl, alkenyl, alkynyl, O=C, HOOC, $H_2NOC$, $R^3OOC$ and/or RO residues and $R^5$ and $R^9$ can be substituted or unsubstituted alkyl, cycloalkyl, aryl, alkenyl, alkynyl, polyhydroxyalkyl or sugar residues, and q is a whole number between 1 and 5. Especially preferably, the residues $R^4$, $R^5$, $R^6$, $R^7$, $R^8$ and $R^9$ can be hydrogen, a methyl or ethyl group, a polyhydroxyalkyl residue or a sugar residue. Likewise preferred is the production of diols, sugar alcohols and polyalcohols that, in a departure from the general formula $R^4H(OH)C$—$(C(OR^5)R^6)q$—$C(OR^9)R^7R^8$, have various residues $OR^{10}$ and $R^{11}$ at nonterminal carbon atoms, independently of one another and in all combinations with each other, where $R^{10}$ can have the same meaning as $R^5$ and $R^{11}$ the meaning of $R^6$.

In a likewise preferred embodiment it is possible for sugar alcohols to be obtained as product. Sugar alcohols is the group name for the polyhydroxy compounds that result from saccharides by reduction or hydrogenation of the carbonyl group. In their open chain form sugars have a C=O group. Thus certain sugars can be seen as aldehydes or ketones and thus in principle can be used as starting material for the method in accordance with the invention. The preferred embodiment includes the sugars in unsubstituted and in substituted form, especially in the form in which other organic residues are bonded to the sugar via one, two, three, four or five hydroxyl groups in the form of an ether, acetal or ester bond.

Particularly preferred embodiments of the method in accordance with the invention are the methods for producing sorbitol from dextrose, a mixture of sorbitol and mannitol from fructose, xylitol from xylose, maltitol from maltose, isomaltitol from isomaltose, dulcitol from galactose and lactitol from lactose, in each case by catalytic hydrogenation of the sugar. However, other sugars can also be hydrogenated to the corresponding sugar alcohols, for example, lactulose, trehalulose, maltulose, isomaltulose, leucrose or starch hydrolyzates. The starting compounds can be highly pure products or components of a mixture that preferably contain at least 80, especially at least 95 wt % of the relevant sugar.

Examples of polyols that can be produced by the method in accordance with the invention and that carry other organic residues via an oxygen, are 1-O-α-D-glucopyrabosyl-D-mannitol, 6-O-α-D-glucopyranosyl-D-sorbitol, which can be prepared in each case from 6-O-α-D-glucopyranosyl-D-fructose, or 3-O-β-D-galactopyranosyl-D-sorbitol, which can be prepared from lactulose.

Regardless of which types of alcohols are supposed to be produced, it is possible in accordance with the invention to produce just one alcohol in a reaction. However, it is also possible by the method in accordance with the invention to produce mixtures of different alcohols. These mixtures can be obtained, for example, by nonselective hydrogenation of starting substances that contain more than one hydrogenatable carbonyl group or through the formation of diastereomers during the reaction or by hydrogenation of mixtures that contain two or more carbonyl compounds.

In each case according to the starting compound it is possible to carry out the method in accordance with the invention in the liquid phase or in the gas phase. The method can be carried out in the liquid phase only if the compound to be hydrogenated is liquid under the reaction conditions. However, in many cases it is preferable to carry out the process in the presence of a solvent. Basically all common solvents can be used, provided they are not degraded during the hydrogenation reaction. Examples of ordinary solvents are water, dioxane, tetrahydrofuran, cyclohexane, methanol, ethanol, n-propanol, isopropanol, n-butanol, cyclohexanol, ethylene glycol, 1,4-butanediol, 1,6-hexanediol, ethylene glycol methyl ether, ethylene glycol ethyl ether, ethylene glycol dimethyl ether or triethylene glycol methyl ether. Mixtures of different solvents are also possible. The presence of one or more solvents can on the one hand result in the operating parameters like pressure and temperature lying in more moderate regions than with a solvent-free process conduct, or to it being possible to conduct the reaction at all. On the other hand, the selectivity of the hydrogenation reaction can be increased through the skilled selection of solvents. In many cases, especially in the production of sugar alcohols, water or water-containing mixtures are preferred.

Because of the great breadth of variation of the possible starting compounds and synthesizable compounds the reaction parameters lie in relatively broad ranges.

The usual pressures at which the method in accordance with the invention is conducted lie in the range from 1 to 450 bar, preferably between 5 and 300 bar. The usual reaction temperatures lie in the range between room temperature and 300° C., preferably between 30° C. and 250° C., especially in the range between 40° C. and 1 80° C. The catalyst load can preferably lie in the range from 0.05 kg to 5 kg of the compound being hydrogenated per kg of catalyst per hour. If the method in accordance with the invention is carried out in a batch process, the weight ratio between the catalyst and the carbonyl compound that is to be hydrogenated preferably lies in the range between 0.01 and 1.

In accordance with the invention the starting compounds are preferably hydrogenated by the following method for the production of polyols, especially sugar alcohols: a 10–70 wt %, preferably 15–50 wt %, especially 40–50 wt % solution of a hydroxyaldehyde or hydroxyketone, preferably a sugar, is prepared in demineralized water. The pH is preferably in the range between 3.0 and 12.0. The pH can be adjusted to the desired value, for example, through the addition of water-soluble basic compounds like alkali carbonates or ammonia in an aqueous solution or acid compounds like sugar acids, sorbic acid or citric acid. This solution is then hydrogenated.

The production of polyalcohols can be carried out in an especially preferred way continuously in a fixed bed process or semicontinuously. The solution to be hydrogenated can be passed through the catalyst bed from above or from below. A cocurrent or countercurrent process can be used, as is known. The catalyst loads, [LHSV, WHSV] can usually lie in the range between 0.05 and 5 kg carbonyl compound per kg of catalyst per hour.

However, the invention also provides for the hydrogenation to be carried out in a suspension process or in a batch process so that the catalyst is fixed in position in a catalyst basket. Suitable reactors for the said types of processes are known from the prior art.

Preferably, hydrogenation is carried out with pure hydrogen at a pressure from 30 to 450 bar, preferably between 30 and 300 bar, and at a temperature in the range between 60 and 150° C., preferably in the range between 70 and 120° C. At higher temperatures there is the danger, particularly when sugars are used as starting compounds, that the sugars will caramelize and deactivate the catalyst. If polyalcohols are produced in a batch process, usually lower pressures are needed, in the range from 30 to 150 bar. With a continuous process, in contrast, higher pressures are used as a rule, because of the lower residence times, which are chiefly in the range from 100 to 300 bar.

The hydrogen is usually added in an at least threefold molar excess. Especially preferred is a mol ratio of hydroxyaldehyde or hydroxyketone to hydrogen from 1:5 to 1:10 with respect to dry substances. By precise adjustment of the ratio of carbonyl compound to hydrogen it is possible to control the product ratios when different stereoisomers can result in a process.

In a continuous process it is also possible to conduct the hydrogenation in two or more steps. For example, the hydrogenation can be carried out in a first step at a temperature in the range between 60 and 90° C. and can be completed in a second step at a temperature from 90 to 140° C. In this way one can prevent, for example, the deactivation of the catalyst through caramelization of the educts, for example, or one can reduce the formation of by products.

The method for producing alcohols by catalytic hydrogenation of carbonyl compounds in accordance with the invention using hollow Raney nickel catalysts has the following advantages:

The hollow Raney catalyst used in accordance with the invention has a distinctly lower bulk density than the previously used Raney catalysts. In this way one needs considerably less catalyst material than in the previously known processes.

In spite of the distinctly lower amount of catalyst material the production of alcohols can be carried out with high conversion rates, very good yields and very good space-time yields.

The catalyst used in the method in accordance with the invention has very good strength. Very good hydrogenation activity that lasts a long time results from this.

Application Example 1

The catalyst activities of the catalysts from Examples 1–6 in the hydrogenation of glucose to sorbitol were compared. For this purpose 20 mL catalyst were put into a tubular reactor and tested in a trickle phase. The reaction temperature was 140° C., the concentration of glucose in the water was 40 wt % and the reaction pressure was 50 bar. The hydrogen throughput was 22.5 L/h and the LHSV was 3 h$^{-1}$. The product mixture was analyzed by HPLC.

EXAMPLE 1

A coating solution was prepared by suspending 1730 g 53% Ni and 47% Al alloy powder (this alloy was melted in an induction oven, poured into a crucible, cooled in air, and ground; the particle size distribution of the powder was <65 μm) and 130 g pure nickel powder (99% Ni, $d_{50}$=21 μm) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 53% Ni and 47% Al alloy powder (this alloy was melted in an induction oven, poured into a crucible, cooled in air, and ground; the particle size distribution of the powder was <65 μm), 90 g pure nickel powder (99% Ni, $d_{50}$=21 μm) and 1083 mL of an aqueous solution containing about 2 wt % polyvinyl alcohol. This suspension was then sprayed onto 1000 mL of the said polystyrene spheres that had been precoated with Ni/Al, while suspending these spheres in an upward-directed air stream (nitrogen and other gases can also be used). After coating the polystyrene spheres with the said solutions, the spheres were heated to 500° C. in order to burn out the polystyrene. The Ni/Al hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.3 mm and a shell thickness of about 700 μm. 20 mL (17.69 g) of this catalyst were tested per Application Example 1; the results of this test are given in Table 1.

TABLE 1

Results of Example 1

| Time (h) | Conversion (%) | Activity (g glucose/mL cat·h) | Activity (g glucose/g cat·h) |
|---|---|---|---|
| 1.73 | 31.00 | 0.43 | 0.49 |
| 3.88 | 24.75 | 0.35 | 0.39 |
| 5.35 | 27.25 | 0.38 | 0.43 |

EXAMPLE 2

A coating solution was prepared by suspending 1730 g 53% Ni and 47% Al alloy powder (this alloy was melted in an induction oven, atomized in water, cooled in air, and ground; the particle size distribution of the powder was <65 μm) and 130 g pure nickel powder (99% Ni, $d_{50}$=21 μm) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 53% Ni and 47% Al alloy powder (this alloy was melted in an induction oven, atomized in water, cooled in air, and ground; the particle size distribution of the powder was <65 μm), 90 g pure nickel powder (99% Ni, $d_{50}$=21 μm) and 1083 mL of an aqueous solution containing about 2 wt % polyvinyl alcohol. This suspension was then sprayed onto 1000 mL of the said polystyrene spheres that had been precoated with Ni/Al, while suspending these spheres in an upward-directed air stream (nitrogen and other gases can also be used). After coating the polystyrene spheres with the said solutions, the spheres were heated to 500° C. in order to burn out the polystyrene. The Ni/Al hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.7 mm and a shell thickness of about 700 μm. 20 mL (13.44 g) of this catalyst were tested per Application Example 1; the results of this test are given in Table 2.

TABLE 2

Results of Example 2

| Time (h) | Conversion (%) | Activity (g glucose/mL cat·h) | Activity (g glucose/g cat·h) |
|---|---|---|---|
| 2.05 | 24.50 | 0.34 | 0.51 |
| 5.25 | 27.50 | 0.38 | 0.57 |

EXAMPLE 3

A coating solution was prepared by suspending 1730 g 53% Ni and 47% Al alloy powder (this alloy was melted in an induction oven, atomized in nitrogen, cooled in air, and ground; the particle size distribution of the powder was <65 μm) and 130 g pure nickel powder (99% Ni, $d_{50}$=21 μm) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 53% Ni and 47% Al alloy powder (this alloy was melted in an induction oven, atomized in nitrogen, cooled in air, and ground; the particle size distribution of the powder was <65 $\mu$m), 90 g pure nickel powder (99% Ni, $d_{50}$=21 $\mu$m) and 1083 mL of an aqueous solution containing about 2 wt % polyvinyl alcohol. This suspension was then sprayed onto 1000 mL of the said polystyrene spheres that had been precoated with Ni/Al, while suspending these spheres in an upward-directed air stream (nitrogen and other gases can also be used). After coating the polystyrene spheres with the said solutions, the spheres were heated to 500° C. in order to burn out the polystyrene. The Ni/Al hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.7 mm and a shell thickness of about 700 $\mu$m. 20 mL (13.44 g) of this catalyst were tested per Application Example 1 and the results of this test are given in Table 3.

TABLE 3

Results of Example 3

| Time (h) | Conversion (%) | Activity (g glucose/mL cat·h) | Activity (g glucose/g cat·h) |
|---|---|---|---|
| 1.95 | 33.25 | 0.47 | 0.69 |
| 5 | 31.50 | 0.44 | 0.66 |

EXAMPLE 4

A free-flowing pelletizable catalyst mixture was prepared in accordance with the instructions in EP 0 648 534 A1 for a catalyst, from 1000 g 50% Ni and 50% Al alloy powder (this alloy was melted in an induction oven and atomized in water), 75 g pure nickel powder (99% Ni, $d_{50}$=21 $\mu$m) and 50 g ethylenebisstearoylamide. Tablets 4 mm in diameter and 4 mm thick were pressed from this mixture. The molded articles were calcined for 2 h at 700° C. After calcination the tablets were activated for 2 h at 80° C. in 20% sodium hydroxide. 20 mL (28.75 g) of this catalyst were tested per Application Example 1 and the results of this test are given in Table 4.

TABLE 4

Results of Example 4

| Time (h) | Conversion (%) | Activity (g glucose/mL cat·h) | Activity (g glucose/g cat·h) |
|---|---|---|---|
| 1.10 | 24.28 | 0.34 | 0.24 |
| 2.68 | 19.50 | 0.28 | 0.19 |
| 4.60 | 23.25 | 0.33 | 0.23 |

EXAMPLE 5

A coating solution was prepared by suspending 1730 g 53% Ni and 47% Al alloy powder (this alloy was melted in an induction oven, poured into a crucible, cooled in air, and ground; the particle size distribution of the powder was <65 $\mu$m) and 130 g pure nickel powder (99% Ni, $d_{50}$=21 $\mu$m) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 53% Ni and 47% Al alloy powder (this alloy was melted in an induction oven, poured into a crucible, cooled in air, and ground; the particle size distribution of the powder was <65 $\mu$m), 90 g pure nickel powder (99% Ni, $d_{50}$=21 $\mu$m) and 1083 mL of an aqueous solution containing about 2 wt % polyvinyl alcohol. This suspension was then sprayed onto 1000 mL of the said polystyrene spheres that had been precoated with Ni/Al, while suspending these spheres in an upward-directed air stream (nitrogen and other gases can also be used). After coating the polystyrene spheres with the said solutions, the spheres were heated to 500° C. in order to burn out the polystyrene. The Ni/Al hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.3 mm and a shell thickness of about 700 $\mu$m. This catalyst was doped with a sodium molybdate solution; the end Mo content of the catalyst was 0.3%. 20 mL (18.74 g) of this catalyst were tested per Application Example 1 and the results of this test are given in Table 5.

TABLE 5

Results of Example 5

| Time (h) | Conversion (%) | Activity (g glucose/mL cat·h) | Activity (g glucose/g cat·h) |
|---|---|---|---|
| 1.70 | 33.75 | 0.47 | 0.51 |
| 4.13 | 27.75 | 0.39 | 0.42 |
| 5.95 | 27.50 | 0.38 | 0.41 |

EXAMPLE 6

A coating solution was prepared by suspending 1730 g 48.5% Ni, 50.1% Al, 0.9% Cr and 0.5% Fe alloy powder (this alloy was melted in an induction oven, poured into a crucible, cooled in air, and ground; the particle size distribution of the powder was <65 $\mu$m) and 130 g pure nickel powder (99% Ni, $d_{50}$=21 $\mu$m) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 48.5% Ni, 50.5% Al, 0.9% Cr and 0.5% Fe alloy powder (this alloy was melted in an induction oven, poured into a crucible, cooled in air, and ground; the particle size distribution of the powder was <63 $\mu$m), 90 g pure nickel powder (99% Ni, $d_{50}$=21 $\mu$m) and 1083 mL of an aqueous solution containing about 2 wt % polyvinyl alcohol. This suspension was then sprayed onto 1000 mL of the said polystyrene spheres that had been precoated with Ni/Al/Cr/Fe, while suspending these spheres in an upward-directed air stream (nitrogen and other gases can also be used). After coating the polystyrene spheres with the said solutions, the spheres were heated to 500° C. in order to burn out the polystyrene. The Ni/Al/Cr/Fe hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.3 mm and a shell thickness of about 700 $\mu$m. This catalyst was doped with an $H_2ReO_4$ solution; the end Re content of the catalyst was 5%. 20 mL (17.59 g) of this catalyst were tested per Application Example 1 and the results of this test are given in Table 6.

TABLE 6

Results of Example 6

| Time (h) | Conversion (%) | Activity (g glucose/mL cat·h) | Activity (g glucose/g cat·h) |
|---|---|---|---|
| 2.18 | 24.95 | 0.35 | 0.40 |
| 3.15 | 23.32 | 0.33 | 0.37 |
| 5.35 | 23.31 | 0.33 | 0.37 |

Application Example 2

The catalyst activities of the catalysts from Examples 7–18 in the hydrogenation of acetone to isopropanol were compared. For this purpose 20 mL catalyst were put into a tubular reactor and tested in a trickle phase. The reaction temperature was 75° C., the reaction was carried out with pure acetone and the reaction pressure was 5 bar. The hydrogen throughput was 120 L/h and the LHSV was 4.1 h$^{-1}$. The product mixture was analyzed by GC.

EXAMPLE 7

A coating solution was prepared by suspending 1730 g 53% Ni and 47% Al alloy powder (this alloy was melted in an induction oven, poured into a crucible, cooled in air, and ground; the particle size distribution of the powder was <25 µm) and 130 g pure nickel powder (99% Ni, d$_{50}$=21 µm) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 53% Ni and 47% Al alloy powder (this alloy was melted in an induction oven, poured into a crucible, cooled in air, and ground; the particle size distribution of the powder was <25 µm), 90 g pure nickel powder (99% Ni, d$_{50}$=21 µm) and 1083 mL of an aqueous solution containing about 2 wt % polyvinyl alcohol. This suspension was then sprayed onto 1000 mL of the said polystyrene spheres that had been precoated with Ni/Al, while suspending these spheres in an upward-directed air stream (nitrogen and other gases can also be used). After coating the polystyrene spheres with the said solutions, the spheres were heated to 500° C. in order to burn out the polystyrene. The Ni/Al hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.7 mm and a shell thickness of about 700 µm. 20 mL (19.59 g) of this catalyst were tested per Application Example 2 and the results of this test are given in Table 7.

EXAMPLE 8

20 mL (17.69 g) of the catalyst from Example 1 were tested per Application Example 2 and the results of this test are given in Table 7.

EXAMPLE 9

20 mL (13.44 g) of the catalyst from Example 2 were tested per Application Example 2 and the results of this test are given in Table 7.

EXAMPLE 10

20 mL (13.44 g) of the catalyst from Example 3 were tested per Application Example 2 and the results of this test are given in Table 7.

EXAMPLE 11

A coating solution was prepared by suspending 1730 g 48% Ni, 49% Al, 1.3% Cr and 1.0% Fe alloy powder (this alloy was melted in an induction oven, poured into a crucible, cooled in air, and ground; the particle size distribution of the powder was <65 µm) and 130 g pure nickel powder (99% Ni, d$_{50}$=21 µm) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 48% Ni, 49% Al, 1.3% Cr and 1.0% Fe alloy powder (this alloy was melted in an induction oven, poured into a crucible, cooled in air, and ground; the particle size distribution of the powder was <65 µm), 90 g pure nickel powder (99% Ni, d$_{50}$=21 µm) and 1083 mL of an aqueous solution containing about 2 wt % polyvinyl alcohol. This suspension was then sprayed onto 1000 mL of the said polystyrene spheres that had been precoated with Ni/Al/Cr/Fe, while suspending these spheres in an upward-directed air stream (nitrogen and other gases can also be used). After coating the polystyrene spheres with the said solutions, the spheres were heated to 500° C. in order to burn out the polystyrene. The Ni/Al/Cr/Fe hollow spheres were then heated to 800° C. in order to sinter the alloy particles and nickel powder together. The hollow spheres were then activated in 20 wt % sodium hydroxide for about 1.5 h at 80° C. The resulting hollow spheres had a diameter of about 6 mm and a shell thickness of about 700 µm. 20 mL (9.48 g) of this catalyst were tested per Application Example 2 and the results of this test are given in Table 7.

EXAMPLE 12

A coating solution was prepared by suspending 1730 g 53% Ni and 47% Al alloy powder (this alloy was melted in an induction oven, poured into a crucible, cooled in air, and ground; the particle size distribution of the powder was <25 µm) and 130 g pure nickel powder (99% Ni, d$_{50}$=21 µm) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 53% Ni and 47% Al alloy powder (this alloy was melted in an induction oven, poured into a crucible, cooled in air, and ground; the particle size distribution of the powder was <25 µm), 90 g pure nickel powder (99% Ni, d$_{50}$=21 µm) and 1083 mL of an aqueous solution containing about 2 wt % polyvinyl alcohol. This suspension was then sprayed onto 1000 mL of the said polystyrene spheres that had been precoated with Ni/Al, while suspending these spheres in an upward-directed air stream (nitrogen and other gases can also be used). After coating the polystyrene spheres with the said solutions, the spheres were heated to 500° C. in order to burn out the polystyrene. The Ni/Al hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 4 mm and a shell thickness of about 700 µm. 20 mL (16.59 g) of this catalyst were tested per Application Example 2 and the results of this test are given in Table 7.

EXAMPLE 13

A coating solution was prepared by suspending 1730 g 53% Ni and 47% Al alloy powder (this alloy was melted in an induction oven, poured into a crucible, cooled in air, and ground; the particle size distribution of the powder was <25 μm) and 130 g pure nickel powder (99% Ni, $d_{50}$=21 μm) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 53% Ni and 47% Al alloy powder (this alloy was melted in an induction oven, poured into a crucible, cooled in air, and ground; the particle size distribution of the powder was <65 μm), 90 g pure nickel powder (99% Ni, $d_{50}$=21 μm) and 1083 mL of an aqueous solution containing about 2 wt % polyvinyl alcohol. This suspension was then sprayed onto 1000 mL of the said polystyrene spheres that had been precoated with Ni/Al, while suspending these spheres in an upward-directed air stream (nitrogen and other gases can also be used). After coating the polystyrene spheres with the said solutions, the spheres were heated to 500° C. in order to burn out the polystyrene. The Ni/Al hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 4 mm and a shell thickness of about 700 μm. 20 mL (16.28 g) of this catalyst were tested per Application Example 2 and the results of this test are given in Table 7.

EXAMPLE 14

A coating solution was prepared by suspending 1730 g 53% Ni and 47% Al alloy powder (this alloy was melted in an induction oven, poured into a crucible, cooled in air, and ground; the particle size distribution of the powder was <65 μm) and 130 g pure nickel powder (99% Ni, $d_{50}$=21 μm) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 53% Ni and 47% Al alloy powder (this alloy was melted in an induction oven, poured into a crucible, cooled in air, and ground; the particle size distribution of the powder was <65 μm), 90 g pure nickel powder (99% Ni, $d_{50}$=21 μm) and 1083 mL of an aqueous solution containing about 2 wt % polyvinyl alcohol. This suspension was then sprayed onto 1000 mL of the said polystyrene spheres that had been precoated with Ni/Al, while suspending these spheres in an upward-directed air stream (nitrogen and other gases can also be used). After coating the polystyrene spheres with the said solutions, the spheres were heated to 500° C. in order to burn out the polystyrene. The Ni/Al hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 4 mm and a shell thickness of about 700 μm. 20 mL (15.86 g) of this catalyst were tested per Application Example 2 and the results of this test are given in Table 7.

EXAMPLE 15

A coating solution was prepared by suspending 1730 g 53% Ni and 47% Al alloy powder (this alloy was melted in an induction oven, poured into a crucible, cooled in air, and ground; the particle size distribution of the powder was <65 μm) and 130 g pure nickel powder (99% Ni, $d_{50}$=21 μm) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 53% Ni and 47% Al alloy powder (this alloy was melted in an induction oven, poured into a crucible, cooled in air, and ground; the particle size distribution of the powder was <25 μm), 90 g pure nickel powder (99% Ni, $d_{50}$=21 μm) and 1083 mL of an aqueous solution containing about 2 wt % polyvinyl alcohol. This suspension was then sprayed onto 1000 mL of the said polystyrene spheres that had been precoated with Ni/Al, while suspending these spheres in an upward-directed air stream (nitrogen and other gases can also be used). After coating the polystyrene spheres with the said solutions, the spheres were heated to 500° C. in order to burn out the polystyrene. The Ni/Al hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 4 mm and a shell thickness of about 700 μm. 20 mL (16.19 g) of this catalyst were tested per Application Example 2 and the results of this test are given in Table 7.

EXAMPLE 16

A coating solution was prepared by suspending 1730 g 53% Ni and 47% Al alloy powder (this alloy was melted in an induction oven, poured into a crucible, cooled in air, and ground; the particle size distribution of the powder was <25 μm) and 130 g pure nickel powder (99% Ni, $d_{50}$=21 μm) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 53% Ni and 47% Al alloy powder (this alloy was melted in an induction oven, poured into a crucible, cooled in air, and ground; the particle size distribution of the powder was <25 μm), 90 g pure nickel powder (99% Ni, $d_{50}$=21 μm) and 1083 mL of an aqueous solution containing about 2 wt % polyvinyl alcohol. This suspension was then sprayed onto 1000 mL of the said polystyrene spheres that had been precoated with Ni/Al, while suspending these spheres in an upward-directed air stream (nitrogen and other gases can also be used). After coating the polystyrene spheres with the said solutions, the spheres were heated to 500° C. in order to burn out the polystyrene. The Ni/Al hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3 mm and a shell thickness of about 700 μm. 20 mL (19.06 g) of this catalyst were tested per Application Example 2 and the results of this test are given in Table 7.

EXAMPLE 17

A free-flowing pelletizable catalyst mixture was prepared in accordance with the instructions in EP 0 648 534 A1 for a catalyst, from 1000 g 50% Ni and 50% Al alloy powder (this alloy was melted in an induction oven and atomized in water), 75 g pure nickel powder (99% Ni, $d_{50}$=21 μm) and 50 g ethylenebisstearoylamide. Tablets 3 mm in diameter and 3 mm thick were pressed from this mixture. The molded articles were calcined for 2 h at 700° C. After calcination the tablets were activated for 2 h at 80° C. in 20% sodium hydroxide. 20 mL (35.1 g) of this catalyst were tested per Application Example 2 and the results of this test are given in Table 7.

EXAMPLE 18

A free-flowing pelletizable catalyst mixture was prepared in accordance with the instructions in EP 0 648 534 A1 for a catalyst, from 1000 g 53% Ni and 47% Al alloy powder (this alloy was melted in an induction oven, poured into a crucible, cooled in air and ground), 150 g pure nickel powder (99% Ni, $d_{50}$=21 μm) and 50 g ethylenebisstearoylamide. Tablets 3 mm in a diameter and 3 mm thick were pressed from this mixture. The molded articles were calcined for 2 h at 700° C. After calcination the tablets were activated for 2 h at 80° C. in 20% sodium hydroxide. 20 mL (42.74 g) of this catalyst were tested per Application Example 2 and the results of this test are given in Table 7.

TABLE 7

The results of the acetone tests

| Example No. | Conversion (%) | Activity (mmol acetone/(g cat·h)) | Selectivity (%) |
| --- | --- | --- | --- |
| 7 | 75.79 | 42.99 | 99.94 |
| 8 | 95.41 | 60.04 | 99.99 |
| 9 | 94.17 | 78.15 | 99.85 |
| 10 | 77.36 | 63.98 | 99.95 |
| 11 | 94.68 | 112.03 | 99.99 |
| 12 | 90.31 | 60.53 | 99.95 |
| 13 | 94.70 | 64.84 | 99.98 |
| 14 | 96.45 | 97.76 | 99.95 |
| 15 | 91.30 | 62.75 | 99.97 |
| 16 | 97.14 | 56.69 | 99.88 |
| 17 | 95.33 | 30.0 | 99.97 |
| 18 | 93.80 | 24.18 | 99.94 |

Application Example 3

The catalytic activities of the catalysts from Examples 19 to 21 in the hydrogenation of maleic anhydirde (MSA) to succinic anhydride (BSA), 1,4-butanediol (BDO), gamma-butyrolactone (GBL) and tetrahydrofuran (THF) were compared. For this purpose 40 mL catalyst were put into a tubular reactor and tested in a trickle phase. The reaction temperature was 195–211° C., the content of MSA in dioxane was 50 wt % and the reaction pressure was 70 bar. The throughput of hydrogen was 60 L/h, the WHSV was from 0.116 to 0.467 $h^{-1}$ and the LHSV was from 0.54 to 2.12 $h^{-1}$. The product mixture was analyzed by GC.

EXAMPLE 19

A coating solution was prepared by suspending 1730 g 40% Ni, 58.5% Al, 1.0% Cr and 0.5% Fe alloy powder (this alloy was melted in an induction oven, poured into a crucible, atomized in water and ground) and 130 g pure nickel powder (99% Ni, $d_{50}$=21 μm) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 40% Ni, 58.5% Al, 1.0% Cr and 0.5% Fe alloy powder (this alloy was melted in an induction oven, poured into a crucible, atomized in water and ground), 90 g pure nickel powder (99% Ni, $d_{50}$=21 μm) and 1083 mL of an aqueous solution containing about 2 wt % polyvinyl alcohol. This suspension was then sprayed onto 1000 mL of the said polystyrene spheres that had been precoated with Ni/Al/Cr/Fe, while suspending these spheres in an upward-directed air stream (nitrogen and other gases can also be used). After coating the polystyrene spheres with the said solutions, the spheres were heated to 500° C. in order to burn out the polystyrene. The Ni/Al/Cr/Fe hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.3 mm and a shell thickness of about 700 μm. This catalyst was doped with an $H_2ReO_4$ solution; the end Re content of the catalyst was 1%. 40 mL (57.02 g) of this catalyst were tested per Application Example 3 and the results of this test are given in Table 8.

TABLE 8

The results of Example 19

| LHSV [$h_{-1}$] | Throughput (g MSA/ (h·mL cat)) | ° C. | Conversion (%) | % BSA | % GBL | % BDO | % THF |
| --- | --- | --- | --- | --- | --- | --- | --- |
| 2.05 | 0.232 | 211 | 100 | 10.8 | 29.6 | 0.5 | 5.5 |
| 2.05 | 0.232 | 211 | 100 | 7.3 | 30.9 | 0.3 | 7.4 |
| 0.54 | 0.231 | 211 | 100 | 4.4 | 32.6 | 0.2 | 5.7 |

EXAMPLE 20

A coating solution was prepared by suspending 1730 g 48.5% Ni, 50.1% Al, 0.9% Cr and 0.5% Fe alloy powder (this alloy was melted in an induction oven, poured into a crucible, cooled in air, and ground; the particle size distribution of the powder was <63 μm) and 130 g pure nickel powder (99% Ni, $d_{50}$=21 μm) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 48.5% Ni, 50.5% Al, 0.9% Cr and 0.5% Fe alloy powder (this alloy was melted in an induction oven, poured into a crucible, cooled in air, and ground; the particle size distribution of the powder was <63 μm), 90 g pure nickel powder (99% Ni, $d_{50}$=21 μm) and 1083 mL of an aqueous solution containing about 2 wt % polyvinyl alcohol. This suspension was then sprayed onto 1000 mL of the said polystyrene spheres that had been precoated with Ni/Al/Cr/Fe, while suspending these spheres in an upward-directed air stream (nitrogen and other gases can also be used). After coating the polystyrene spheres with the said solutions, the spheres were heated to 500° C. in order to burn out the polystyrene. The Ni/Al/Cr/Fe hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.3 mm and a shell thickness of about 700 μm. This catalyst was doped with an $H_2ReO_4$ solution; the end Re content of the catalyst was 1.5%. 40 mL (37.75 g) of this catalyst were tested per Application Example 3 and the results of this test are given in Table 9.

TABLE 9

The results of Example 20

| LHSV [$h_{-1}$] | Throughput (g MSA/ (h·mL cat)) | °C. | Conversion (%) | % BSA | % GBL | % BDO | % THF |
|---|---|---|---|---|---|---|---|
| 2.015 | 0.116 | 195 | 100 | 1.5 | 66.1 | 0.0 | 1.8 |

EXAMPLE 21

A coating solution was prepared by suspending 1730 g 48.5% Ni, 50.1% Al, 0.9% Cr and 0.5% Fe alloy powder (this alloy was melted in an induction oven, poured into a crucible, cooled in air, and ground; the particle size distribution of the powder was <63 µm) and 130 g pure nickel powder (99% Ni, $d_{50}$=21 µm) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 48.5% Ni, 50.5% Al, 0.9% Cr and 0.5% Fe alloy powder (this alloy was melted in an induction oven, poured into a crucible, cooled in air, and ground; the particle size distribution of the powder was <63 µm), 90 g pure nickel powder (99% Ni, $d_{50}$=21 µm) and 1083 mL of an aqueous solution containing about 2 wt % polyvinyl alcohol. This suspension was then sprayed onto 1000 mL of the said polystyrene spheres that had been precoated with Ni/Al/Cr/Fe, while suspending these spheres in an upward-directed air stream (nitrogen and other gases can also be used). After coating the polystyrene spheres with the said solutions, the spheres were heated to 500° C. in order to burn out the polystyrene. The Ni/Al/Cr/Fe hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.3 mm and a shell thickness of about 700 µm. This catalyst was doped with an $H_2ReO_4$ solution; the end Re content of the catalyst was 5%. 40 mL (37.75 g) of this catalyst were tested per Application Example 3 and the results of this test are given in Table 10.

TABLE 10

The results of Example 21

| LHSV [$h_{-1}$] | Throughput (g MSA/ (h·mL cat)) | °C. | Conversion (%) | % BSA | % GBL | % BDO | % THF |
|---|---|---|---|---|---|---|---|
| 2.017 | 0.117 | 195 | 100 | 39.9 | 51.9 | 0.1 | 1.4 |
| 2.04 | 0.233 | 195 | 100 | 42.6 | 53.6 | 0.0 | 0.1 |
| 2.112 | 0.463 | 196 | 100 | 51.8 | 42.3 | 0.0 | 0.2 |
| 2.12 | 0.467 | 210 | 100 | 38.8 | 52.6 | 0.0 | 0.6 |

Application Example 4

The catalytic activities of the catalysts of Examples 22–24 in the hydrogenation of fatty acid methyl esters to fatty alcohols were compared. For this purpose 72 g of the catalyst were put into a basket in an autoclave and tested in liquid phase. The reaction temperature was 200° C. and the amount of the fatty acid methyl ester was 500 mL. This solution was stirred at 1000 rpm and the reaction pressure was 200 bar. The product mixture was analyzed by GC.

EXAMPLE 22

A free-flowing pelletizable catalyst mixture was prepared in accordance with the instructions in EP 0 648 534 Al for a catalyst, from 1000 g 53% Ni and 47% Al alloy powder (this alloy was melted in an induction oven and ground), 150 g pure nickel powder (99% Ni, $d_{50}$=21 µm) and 50 g ethylenebisstearoylamide. Tablets 3 mm in diameter and 3 mm thick were pressed from this mixture. The molded articles were calcined for 2 h at 700° C. After calcination the tablets were activated for 2 h at 80° C. in 20% sodium hydroxide. This catalyst was doped with an $H_2ReO_4$ solution; the end Re content of the catalyst in the end was 3%. 72 g of this catalyst were tested per Application Example 4 and the results of this test are given in Table 11.

TABLE 11

The results of Example 22

| Time (h) | 0 | 3 | 5 | 20.5 |
|---|---|---|---|---|
| Saponification number | 191.5 | 132 | 116 | 33 |
| C-16 esters (%) | 4.95 | 3.47 | 2.91 | 0.31 |
| C-16 alcohol (%) | 0 | 1.36 | 1.82 | 3.42 |
| C-16 conversion (%) | — | 29.8 | 41.1 | 93.7 |
| C-16 selectivity (%) | — | 93.8 | 90.5 | 74.2 |
| C-18 saturated esters (%) | 77.82 | 66.58 | 57.45 | 6.93 |
| C-18 monounsaturated esters (%) | 10.08 | 0.12 | 0.12 | 0.04 |
| C-18 alcohol (%) | 0.26 | 21.27 | 29.07 | 61.75 |
| C-18 conversion (%) | — | 24.1 | 34.5 | 92.07 |
| C-18 selectivity (%) | — | 100 | 95.8 | 76.3 |

EXAMPLE 23

A coating solution was prepared by suspending 1730 g 48.5% Ni, 50.1% Al, 0.9% Cr and 0.5% Fe alloy powder (this alloy was melted in an induction oven, poured into a crucible, cooled in air, and ground; the particle size distribution of the powder was <63 µm) and 130 g pure nickel powder (99% Ni, $d_{50}$=21 µm) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 48.5% Ni, 50.5% Al, 0.9% Cr and 0.5% Fe alloy powder (this alloy was melted in an induction oven, poured into a crucible, cooled in air, and ground; the particle size distribution of the powder was <63 µm), 90 g pure nickel powder (99% Ni, $d_{50}$=21 µm) and 1083 mL of an aqueous solution containing about 2 wt % polyvinyl alcohol. This suspension was then sprayed onto 1000 mL of the said polystyrene spheres that had been precoated with Ni/Al/Cr/Fe, while suspending these spheres in an upward-directed air stream (nitrogen and other gases can also be used). After coating the polystyrene spheres with the said solutions, the spheres were heated to 500° C. in order to burn out the polystyrene. The Ni/Al/Cr/Fe hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.3 mm and a shell thickness of about 700 µm. This catalyst was doped with an $H_2ReO_4$ solution; the end Re content of the catalyst was 3%.

72 g of this catalyst were tested per Application Example 4 and the results of this test are given in Table 12.

TABLE 12

The results of Example 23

| Time (h) | 0 | 1 | 20.5 |
|---|---|---|---|
| Saponification number | 191.5 | — | 20.7 |
| C-16 esters (%) | 5.02 | 4.86 | 0.18 |
| C-16 alcohol (%) | 0 | 0.15 | 4.04 |
| C-16 conversion (%) | — | 3.2 | 96.4 |
| C-16 selectivity (%) | — | 93.75 | 83.5 |
| C-18 saturated esters (%) | 79.13 | 82.16 | 3.42 |
| C-18 monounsaturated esters (%) | 10.25 | 4.18 | 0.81 |
| C-18 alcohol (%) | 0.26 | 2.41 | 68.80 |
| C-18 conversion (%) | — | 3.4 | 95.3 |
| C-18 selectivity (%) | — | 79.3 | 80.8 |

EXAMPLE 24

A coating solution was prepared by suspending 1730 g 48.5% Ni, 50.1% Al, 0.9% Cr and 0.5% Fe alloy powder (this alloy was melted in an induction oven, poured into a crucible, cooled in air, and ground; the particle size distribution of the powder was <63 $\mu$m) and 130 g pure nickel powder (99% Ni, $d_{50}$=21 $\mu$m) in 1557 mL of an aqueous solution containing about 2 wt % polyvinyl alcohol. This suspension was then sprayed onto 1000 mL of polystyrene spheres about 2 mm in diameter, while suspending the spheres in an upward-directed air stream. 1 L of these spheres was further coated with an alloying solution. The solution for the second layer consisted of 1203 g 48.5% Ni, 50.5% Al, 0.9% Cr and 0.5% Fe alloy powder (this alloy was melted in an induction oven, poured into a crucible, cooled in air, and ground; the particle size distribution of the powder was <63 $\mu$m), 90 g pure nickel powder (99% Ni, $d_{50}$=21 $\mu$m) and 1083 mL of an aqueous solution containing about 2 wt % polyvinyl alcohol. This suspension was then sprayed onto 1000 mL of the said polystyrene spheres that had been precoated with Ni/Al/Cr/Fe, while suspending these spheres in an upward-directed air stream (nitrogen and other gases can also be used). After coating the polystyrene spheres with the said solutions, the spheres were heated to 500° C. in order to burn out the polystyrene. The Ni/Al/Cr/Fe hollow spheres were then heated to 800° C. in order to sinter the alloy particles and nickel powder together. The hollow spheres were then activated in 20 wt % sodium hydroxide for about 1.5 h at 80° C. The resulting activated hollow spheres had a diameter of about 3.3 mm and a shell thickness of about 700 $\mu$m. This catalyst was doped with an $H_2ReO_4$ solution; the end Re content of the catalyst was 4.5%. 72 g of this catalyst were tested per Application Example 4 and the results of this test are given in Table 13.

TABLE 13

The results of Example 24

| Time (h) | 0 | 1 | 3 | 5 | 20.5 |
|---|---|---|---|---|---|
| Saponification number | 191.5 | 180 | 159 | 146 | 20.5 |
| C-16 esters (%) | 5.02 | 4.71 | 4.31 | 3.89 | 0.51 |
| C-16 alcohol (%) | 0 | 0.22 | 0.64 | 0.95 | 3.87 |
| C-16 conversion (%) | — | 6.18 | 14.1 | 22.5 | 89.8 |
| C-16 selectivity (%) | — | 70.97 | 90.1 | 84.1 | 85.8 |
| C-18 saturated esters (%) | 79.13 | 79.45 | 79.84 | 73.07 | 10.52 |
| C-18 monounsaturated esters (%) | 10.25 | 5.05 | 0.17 | 0.27 | 0.07 |

TABLE 13-continued

The results of Example 24

| Time (h) | 0 | 1 | 3 | 5 | 20.5 |
|---|---|---|---|---|---|
| C-18 alcohol (%) | 0.26 | 3.06 | 9.27 | 14.45 | 68.05 |
| C-18 conversion (%) | — | 5.5 | 10.5 | 17.95 | 88.2 |
| C-18 selectivity (%) | — | 62.7 | 98.9 | 90.1 | 86.4 |

What is claimed is:

1. A method for producing alcohols comprising reacting a carbonyl compound in a catalytic hydrogenation reaction with hydrogen or hydrogen-containing gases in the presence of a molded hydrogenation Raney catalyst wherein the Raney catalyst is in the form of hollow bodies.

2. The method according to claim 1, wherein the hollow Raney catalyst contains a member selected from the group consisting of nickel, cobalt, copper, iron, platinum, palladium, ruthenium and mixtures thereof as a catalytically active component.

3. The method according to claim 1 wherein the Raney catalyst is in the form of hollow spheres.

4. The method according to claim 2, wherein the Raney catalyst is in the form of hollow spheres.

5. The method according to claim 1, wherein the bulk density of the Raney catalyst according to used is in the range of 0.3 g/mL to 1.3 g/mL.

6. The method according to claim 2, wherein the bulk density of the Raney catalyst according to used is in the range of 0.3 g/mL to 1.3 g/mL.

7. The method according to claim 1, wherein the molded catalyst has a diameter in the range from 0.05 to 20 mm.

8. The method according to claim 1, wherein the molded catalyst has a shell thickness in the range of 0.05–5 mm.

9. The method according to claim 1, wherein the molded catalyst has a shell thickness in the range of 0.1 to 5 mm.

10. The method according to claim 1, wherein the molded catalyst contains an inorganic binder.

11. The method according to claim 1, wherein the molded catalyst does not contain any binder.

12. The method according to claim 1 wherein the catalyst is a cobalt catalyst that is doped with one or more of the elements from groups 3B though 7B, 8 and 1B of the Periodic Table Elements.

13. The method according to claim 1 wherein the catalyst is a cobalt catalyst that is doped with one or more of chromium, manganese, iron, vanadium, tantalum, titanium, tungsten, molybdenum, rhenium and/or metals of the platinum group.

14. The method according to claim 1, wherein the catalyst is a cobalt catalyst doped with one or more of the elements from groups 1A, 2A, 2B and/or 3A of the Periodic Table of Elements and/or germanium, tin, lead, antimony or bismuth.

15. The method according to claim 1 further comprising carrying out the hydrogenation in continuous operation in a fixed bed or suspension reactor.

16. The method according to claim 1, further comprising carrying out the hydrogenation in a batch process.

17. The method according to claim 1, further comprising recovering an alcohols having the formula $R^1 R^2CH—OH$, where $R^1$ and $R^2$, independent of one another, are at least one of aliphatic and aromatic, unbranched and branched, substituted and unsubstituted, saturated and unsaturated residues, or hydrogen.

18. The method according to claim 17, wherein the alcohol has the formula $R^1 R^2CH—OH$, where $R^1$ and $R^2$, independent of one another, are methyl, ethyl, n-propyl, isopropyl, n-butyl, isobutyl, tert-butyl, n-pentyl, isopentyl, n-heptyl, n-octyl, isoctyl, n-nonyl, n-decyl, n-undecyl, n-dodecyl residues or residues of the general $H_3C-(CH_2)_n$, where n is a whole number from 11 to 30, or hydrogen.

19. The method according to claim 17, wherein the residues $R^1$ and/or $R^2$ are substituted with one or more residues from the series F, Cl, Br, I, $NO_2$, $NH_2$, OH, CN, alkyl, aryl, alkenyl, alkynyl, O=C, HOOC, $H_2NOC$, ROOC, RO with R=alkyl, aryl, alkenyl or alkynyl.

20. The method according to claim 18, wherein the residues $R^1$ and/or $R^2$ are substituted with one or more residues from the series F, Cl, Br, I, $NO_2$, $NH_2$, OH, CN alkyl, aryl, alkenyl, alkynyl, O=C, HOOC, $H_2NOC$, ROOC, RO with R=alkyl, aryl, alkenyl or alkynyl.

21. The method according to claim 17, wherein the alcohol contains two or more hydroxyl groups.

22. The method according to claim 17, the alcohol has the formula $Ar(CH_2)_m CR^3H-OH$, where Ar is a mononuclear aromatic residue substituted zero, one, two, three, four or five times or a polynuclear aromatic residue substituted in any way, m is a whole number between 0 and 20 and $R^3$ is a substituted or unsubstituted alkyl, cycloalkyl, aryl, alkenyl or alkynyl residue.

23. A method according to claim 21, wherein diols of the general formula $HO-(CH_2)p-OH$ are obtained, where p is a whole number between 2 and 30.

24. A method according to claim 21, wherein diols of the general formula $HO-(CH_2)p-OH$ are obtained, where p=2, 3, 4, 5, 6, 7 and 8.

25. The method according to claim 21, wherein sugar alcohols are obtained as products.

26. The method according to claim 1, further comprising recovering sugar alcohols from the hydrogenation of ketoses, aldoses or a mixture of ketoses and aldoses.

27. The method according to claim 1, further comprising recovering sorbitol from the hydrogenation of dextrose.

28. The method according to claim 1, further comprising recovering sorbitol from the hydrogenation of a mixture of sorbitol and mannitol from fructose.

29. The method according to claim 1, further comprising recovering xylitol from the hydrogenation of xylose.

30. The method according to claim 1, further comprising recovering maltitol from the hydrogenation of maltose.

31. The method according to claim 1, further comprising recovering isomaltitol from the hydrogenation of isomaltose.

32. The method according to claim 1, further comprising recovering dulcitol from the hydrognation of galactose.

33. The method according to claim 1, further comprising recovering lactitol from the hydrogenation of lactose.

34. The method according to claim 1, further comprising recovering fatty alcohols from the hydrogenation of fatty acid methyl esters.

35. The method according to claim 1, further comprising recovering BSA, GBL, BDO and/or THF from the hydrogenation of MSA.

* * * * *